United States Patent [19]

Weimer et al.

[11] 4,283,514

[45] Aug. 11, 1981

[54] CHEMICALS FOR TERMINATION OF POLYVINYLCHLORIDE POLYMERIZATIONS

[75] Inventors: Dean R. Weimer; Charles M. Starks, both of Ponca City, Okla.

[73] Assignee: Conoco, Inc., Ponca City, Okla.

[21] Appl. No.: 68,819

[22] Filed: Aug. 22, 1979

Related U.S. Application Data

[62] Division of Ser. No. 969,742, Dec. 14, 1978, Pat. No. 4,229,598.

[51] Int. Cl.$^3$ ............................ C08F 2/42; C08K 5/13
[52] U.S. Cl. ............................... 526/84; 260/45.95 H; 568/790; 568/792; 568/793; 568/804
[58] Field of Search ................... 526/84; 260/45.95 H; 568/790, 792, 793, 804, 787, 785, 788

[56] References Cited

U.S. PATENT DOCUMENTS

| | | | |
|---|---|---|---|
| 2,514,363 | 7/1950 | Banes et al. | 526/84 |
| 3,985,721 | 10/1976 | Petit | 526/84 |
| 3,989,665 | 11/1976 | Hollingshead | 260/45.95 H |
| 4,059,563 | 11/1977 | Goto et al. | 260/45.95 H |

FOREIGN PATENT DOCUMENTS 52-3681  1/1977  Japan ......................... 526/84

*Primary Examiner*—John Kight, III
*Attorney, Agent, or Firm*—Cortlan R. Schupbach, Jr.

[57] ABSTRACT

Butylation of a mixture of xylenols and trimethylphenols gives a product which is suitable for use as a stabilizer for polyvinyl chloride. The material can be added to the reactor during polymerization as a shortstopper and retain effectiveness as a stabilizer in the finished polymer.

4 Claims, No Drawings

CHEMICALS FOR TERMINATION OF POLYVINYLCHLORIDE POLYMERIZATIONS

This application is a divisional of Ser. No. 969,742, filed Dec. 14, 1978, now U.S. Pat. No. 4,229,598.

This invention relates to a composition useful as a polyvinyl chloride stabilizer and polymerization shortstopper. More particularly, this invention relates to a compound useful as PVC stabilizer and shortstopper which is obtained from the butylation of a fractionation cut from the product of vapor phase methylation of phenol.

The use of stabilizer and shortstoppers in polyvinyl chloride polymerizations has long been known. A commonly used stabilizer is 2,6-di-tert-butyl 4-methylphenol. Other commonly known stabilizers are shown in U.S. Pat. No. 3,258,449, which shows thioethers in combination with phenolic stabilizers to give the synergistic effect; U.S. Pat. Nos. 2,997,455, which shows 2-tert-butyl 4-methylphenol, as does 3,600,355 and 3,476,698. U.S. Pat. No. 3,499,881 shows the use of 2,6-di-tert-butyl p-cresol as a stabilizer as does U.S. Pat. No. 3,533,991. U.S. Pat. No. 3,454,525 shows polyalpha olefin compositions with synergistic stabilizer combinations of dialkyl esters of 3-thiodipropionic acid and substituted phenols. U.S. Pat. No. 3,535,277 shows natural rubbers stabilized against discoloration and oxidegradation using tertiary alkylated phenols. These examples are representative but far from exhaustive of the phenolic stabilization art.

Many agents have been taught to be useful for terminating free radical polymerizations, such as that of polyvinyl chloride. The prior art does not deal with the use of phenols for this purpose, although bisphenol-A tert-octyl derivatives together with hydroquinone have been used for the shortstopping of vinyl chloride as shown in Czechoslovakian patent 129,314. However, *Emulsion Polymerization of High Polymers,* Volume 9, Interscience Publishers, 1955 page 357, states that several hundred organic compounds were tested and hydroquinone was found to be effective as a shortstopper in GRS in low amounts, indicating that hydroquinone was the active ingredient.

Thus the art amply illustrates that polyvinyl chloride (PVC) polymers are subject to thermal, photochemical and oxidative degradation during production and processing. This degradation greatly reduces the mechanical properties of the polyvinyl chloride, also affecting clarity and color which are esthetic properties valuable in the final products. Thermal decomposition is particularly troublesome with these polymers.

Polyvinyl chloride polymers are subjected to elevated temperatures at various points in their production and processing into finished products. Since vinyl chloride monomer was determined to be a carcinogen, the resins are subjected to elevated temperatures to remove residual vinyl chloride monomer (VCM) after polymerization at temperatures of above 200° F. while using inert gas or steam. Slurry water remaining is removed by centrifuging. The wet cake is dried in a rotary or fluid bed drier where the temperature exceeds the boiling point of water.

In order to produce consistently high quality resin the degradations incurred during the above process steps must be minimized. Conventional stabilizers used for addition to slurry prior to removal of residual VCM and subsequent steps to prevent thermal degradation are normally hindered phenol derivatives such as butylated hydroxy toluene. Modifications of this system are also known. While these products prevent thermal degradation, many of these products have adverse color effects because of thermal degradation products of the phenolic additives themselves. As these products break down, they also lose stabilizing ability and thus are not as effective as desired.

During polymerization of vinyl chloride monomer, it is desirable to stop all polymerization before all monomer present is converted to polymer. If polymerization is allowed to go to completion, finished properties of the polymer produced are severely and adversely affected. Normally, desired levels of conversion are between 70 and 90%. Current methods for terminating polymerization include adding agents (called shortstop agents) to stop free radical propagation, then removing the unreacted monomer and processing the converted slurry to obtain the dry polyvinyl chloride. There are a number of known shortstop agents useful for terminating polymerization. Most are not as effective as desired or they cause adverse effects such as color formation in the polymer.

It would therefore be of great benefit to provide an agent which is both a heat stabilizer and an effective agent for shortstopping polymerization reactions such that simple addition of the agent to the polymerization reactor during polymerization will effectively stop free radical propagation while allowing the agent to remain in the polymer as a heat stabilizer during subsequent processing.

It is therefore an object of the instant invention to provide a shortstopping and stabilizing mixture. Other objects will become apparent to those skilled in this art as the description proceeds.

It has now been discovered according to the instant invention that a heat stabilizer and free radical inhibitor for polyvinyl chloride polymerization can be prepared by a process comprising (1) methylating phenol with methanol in vapor phase at pressures of from about 1 to about 2500 pounds per square inch gauge, temperatures of from about 230° C. to about 500° C., and a liquid hourly space velocity of from about 1 to about 5 while in the presence of alumina or an alumina-containing catalyst, and recovering a product stream therefrom;

(2) distilling said product stream into the desired fractions and retaining a fraction obtained at temperatures of from about 205° C. to about 230° C. at one atmosphere pressure and then;

(3) alkylating the retained fraction with acidic catalysts at temperatures of from about 10° C. to about 110° C. and pressures of at least atmospheric, while at a product fraction/alkylating agent weight ratio of from about 1/0.23 to about 1/1.85 respectively then;

(4) fractionally distilling the product of (3) and retaining the fraction obtained at temperatures of from about 110° C. to about 200° C. at 30 millimeters of mercury.

Normally, the acidic catalyst used for the alkylation of the retained fraction is selected from the group consisting of sulfuric acid, or sulfonic acids such as benzene sulfonic acid, or sulfonated polystyrene resins crosslinked with divinylbenzene, sulfonated polystyrene acidic catalysts and boron trifluoride etherates. Normally the alkylating agents used are those such as isobutylene, isooctene, isohexene, isopentylene, cyclohexene, cyclopentene.

The product fraction of 205° C. to 230° C. is obtained from the methylation of phenols by reaction with methanol over alumina to give a mixture of phenolic products from which various pure compounds and mixtures of compounds are obtained by fractional distillation. The product stream of such a methylation affords a distillation cut in the boiling range of about 210° to 225° C., which contains a high proportion of xylenols and some trimethylphenols. The amount of each of the components present will depend upon the nature of the methylation catalyst used, together with the reaction conditions of the methylation, and the temperature range (cut point) used in the fractional distillation. Minor amounts of other materials may be present in any distillation fraction. The product obtained and described in the instant invention is a result of the methylation of phenol at pressures of from 10 to 50 pounds per square inch gauge, temperatures of 450° to 700° C. and a liquid hourly space velocity of 1 to 5. The catalyst used is an alumina derived from the hydrolysis of aluminum alkoxide, Trademark of and sold by Continental Oil Company as CATAPAL alumina. A mole ratio of methanol to phenol of from about 0.4 to 0.8 is used.

The product stream from the methylation of phenol has the following general composition;

| | |
|---|---|
| o-cresol | 23-30% |
| m,p-cresol | 1-2% |
| 2,6-xylenol | 6-11% |
| 2,4/2,5-xylenol | 1-3% |
| 2,3-xylenol | .5-1.0% |
| 2,4,6-trimethylphenol | 0.3-1.0% |
| 2,3,6-trimethylphenol | 1.0-2.0% |
| (2,3,5)(2,3,4)(2,3,5) trimethylphenols | tr-0.4% |
| Pentamethylbenzene | tr-0.3% |
| Tetramethylphenols | 0.3-1.1% |
| Pentamethylphenol | .2-1.0% |

The fraction which is alkylated is the mixture of cresylic acids that distills between 2,6-xylenol and 2,3,6-trimethylphenol (about 205° C. to about 230° C.). Typical composition of such a fraction is as follows:

| | |
|---|---|
| Phenol | Trace |
| o-cresol | 0.6 w/o |
| m,p-cresol | 0.3 |
| 2,6-xylenol | 9.6 |
| 2,4/2,5-xylenol | 41.8 |
| 2,3-xylenol | 15.6 |
| 2,4,6-trimethylphenol | 27.1 |
| 2,3,6-trimethylphenol | 2.8 |
| 2,3,5/2,4,5-trimethylphenol | 0.1 |
| pentamethylbenzene | 2.1 |

The product of the instant invention is that portion of the reaction mixture from the alkylation of the above fraction which boils at 110°-210° C. at 30 millimeters of mercury. Phenol and unreacted xylenols are removed in a precut to the desired fraction.

Briefly described, the process comprises charging methanol and phenol as vapors into a reactor using alumina as a catalyst. The reaction is exothermic and heat is removed. The conversion of phenol is about 50% per pass. The reaction product is charged to a dehydrator where the water of reaction is removed. The dry cresylic acid product is then pumped to distillation.

Phenol is taken overhead in a first tower and recycled back to the reaction. Ortho-cresol is then taken overhead in a second tower and a 2,6-xylenol fraction is removed in a third tower. Essentially all of the meta, para-cresol produced is taken overhead with 2,6-xylenol. The bottoms from the 2,6 tower are accumulated in storage during the above operation and then can be redistilled, or rerun if desired during which time finer cuts are taken. In the "rerun" operation, accumulated bottoms from the 2,6-xylenol tower are charged to the first tower and 2,6-xylenol is taken overhead. In the second tower, the crsylic acid mixture to be butylated is taken overhead, the fraction containing 2,4/2,5 xylenol, 2,3-xylenol and 2,3,6-trimethylphenol with a small amount of pentamethylbenzene and 2,6-xylenol. In a third tower, crude 2,3,6-trimethylphenol is taken overhead. Bottoms residue from the third tower is useful as a fuel.

Studies were carried out to determine the composition of this material when butylated and to determine differences in composition among various samples having varying antioxidant efficiencies in polyvinyl chloride. While the majority of the components present in this material have been identified, the composition tends to vary as does antioxidant activity. It appears that the varying antioxidant activity cannot be accounted for in terms of the level of any one component of the butylated mixture. It is therefore apparent that several components of the butylated mixture are active as antioxidants and provide a synergism to the system.

Experiments were carried out in which 2,5-xylenol, a mixture of 2,4 and 2,5-xylenols, 2,3-xylenol, and 2,3,6-trimethylphenol were separately butylated in order to determine what proportion of activity of the butylated mixture of the instant invention derive from each of these individual components. Components of the samples were identified using gas chromatographic spectroscopy mass spectralanalysis, nuclear magnetic resonance, and gas chromatographic retention time comparisons.

The butylated mixture is a complex mixture of butylated phenolic compounds, some of which are hindered (hydroxyl groups sterically hindered by an ortho tertiary alkyl group) and others are relatively nonhindered phenols. The literature of antioxidants abounds with examples for a synergism occurring between two phenols where one is hindered and one unhindered or relatively unhindered. For example, the combination of para-methoxyphenol and 2,6-di-tert-butyl-para-cresol (butylated hydroxy toluene or BHT) is a more potent antioxidant than either individually. In the instant invention several samples enriched in one or more of the butylated components have shown poorer antioxidant performance in polyvinyl chloride than the gross mixture itself. Therefore it is apparent that synergism plays a role in the system although no definitive proof is available since the system is so complex. Gas chromatographic analysis of butylated samples using various catalysts for the butylation is shown in Table 1 below. The components which could be identified are so identified although several unknown components have not been determined. In sample 1, Amberlyst 15 ® is a crosslinked sulfonated polystyrene resin using divinyl benzene crosslinking, Trademark of and sold by Rohm and Haas Company.

In the table, the following abbreviations are consistent; xy=xylenol, tmp=trimethylphenol; PMB=pentamethylbenzene. All other known components are substituted phenols and are designated using M as a methyl group and B a t-butyl group. Thus, 2,4-M-6-B is 6-t-butyl 2,4-dimethylphenol. Components that are unidentified are designated with the letter U. Results are reported as area percentages determined by gas chromatographic analysis using a flame detector.

TABLE 1

GAS CHROMATOGRAPHIC ANALYSIS OF BUTYLATED SAMPLES

| Sample | 1 | 2 | 3 | 4 |
|---|---|---|---|---|
| Catalyst | Amberlyst 15 | $BF_3 \cdot Et_2O$ | $BF_3 \cdot Et_2O$ | $H_2SO_4$ |
| Component | (AREA PERCENTAGES) | | | |
| $C_4H_8$ Trimer | .00 | .14 | .02 | .00 |
| $C_4H_8$ Trimer | .00 | .33 | .05 | .11 |
| 2,4-/2,5-Xy | 4.69 | .76 | .00 | .00 |
| 2,3-Xy | 2.50 | .54 | .12 | .00 |
| 2,4,6-TMP | 11.76 | 15.71 | 11.13 | 19.15 |
| 2,3,6-TMP | 2.35 | .55 | .41 | .59 |
| U1 | .96 | .00 | .00 | .00 |
| PMB | 2.07 | 2.20 | .68 | 1.37 |
| U2 | .00 | 1.07 | .15 | .05 |
| 2-M—4-B | .12 | .73 | .08 | .00 |
| U3 | .14 | .36 | .03 | .04 |
| 2,4-M—6-B | 24.07 | 23.60 | 27.64 | 25.47 |
| 2,6-M—4-B | 6.21 | 9.71 | 8.98 | 7.84 |
| 2,3-M—6-B | 22.66 | 17.78 | 21.01 | 5.74 |
| 2,5-M—6-B | .08 | .11 | .09 | .15 |
| 2,3-M—5-B | .00 | .08 | .05 | .00 |
| 2,5-M—4-B | 17.83 | 18.43 | 24.71 | 13.15 |
| 4-M—2,6-B | .00 | .00 | .00 | .05 |
| U4 | .00 | .88 | .06 | .78 |
| U5 | .12 | .00 | .00 | .00 |
| 2,5-M—4,6-B | .64 | .33 | .48 | 5.40 |
| 2,3,6-M—4-B | .56 | .73 | 1.03 | 2.64 |
| U6 | .00 | .26 | .00 | .00 |
| U7 | .00 | .00 | .19 | .00 |
| U8 | .10 | .30 | .33 | .51 |
| U9 | .06 | .21 | .38 | .12 |
| 2,3-M—4,6-B | 2.87 | 4.66 | 1.54 | 16.34 |
| U10 | .00 | .00 | .41 | .00 |

The invention is more concretely described with reference to the examples below wherein all parts and percentages are by weight unless otherwise specified. The examples are provided to illustrate the instant invention and not to limit it. In comparative examples, 2,4,6- and 2,3,6-trimethyphenols were commercially available compounds. References to cresylic acid indicates the pre-alkylation fractionation of the instant invention.

EXAMPLE 1

Cresylic acid (500 grams) and 15 grams of boron trifluoride etherate were charged to a 1 liter flask fitted with a mechanical stirrer, gas inlet tube, thermometer and a reflux condenser. Isobutylene was added through the gas inlet tube with vigorous stirring and at such a rate that all of the gas was consumed a rapidly as added. As the reaction progressed, the heat liberated caused the temperature of the reaction mixture to rise from 22° C. to 82° C. over a period of about 1 hour.

The flow of isobutylene was continued for an additional 2½ hours during which time the temperature dropped to 35° C. The reaction product was washed with water, sodium carbonate solution, and then shaken with anhydrous sodium carbonate. The crude organic product (658 grams) plus about ½ gram of sodium hydroxide was transferred to a distillation flask and fractionally distilled into 4 cuts with the composition shown in Table 2.

TABLE 2

COMPOSITION OF DISTILLATION CUTS FROM BUTYLATION OF CA-450

| Cut No. | 1 | 2 | 3 | 4 |
|---|---|---|---|---|
| Boiling range, °C., at 30mm Hg | 20–105 | 105–135 | 135–155 | 155–180 |
| Weight, grams | 64.6 | 134.1 | 314.5 | 108.5 |
| Composition, % | | | | |
| Isobutylene dimer and trimer | 77.1 | 1.2 | — | — |
| 2,4/and 2,5 xylenol | 9.4 | 18.0 | 0.2 | 0.6 |
| 2,4,6-trimethylphenol | 7.7 | 47.0 | 1.9 | 0.1 |
| 2,3,6-trimethylphenol | 1.2 | 8.6 | 0.8 | 0.2 |
| Pentamethylbenzene | 2.5 | 7.1 | 0.5 | 0.1 |
| Butylated products | 1.7 | 17.2 | 96.4 | 98.9 |
| 2,3,5-/2,4,5-trimethylphenol | 0.4 | 0.8 | 0.2 | 0.1 |

EXAMPLE 2

The experiment of Example 1 was repeated except that the main product was taken overhead in one fraction having a boiling point between 105° and 212° C. at 30 millimeters mercury, rather than being separated into several distillation cuts.

EXAMPLE 3

A mixture containing 49% 2,4-xylenol and 51% 2,5-xylenol was butylated according to the procedure described in Example 1. The product from this reaction was fractionally distilled. Two cuts were taken from the product. Cut A, rich in 2,4-dimethyl 6-t-butylphenol, and Cut B, rich in 2,5-dimethyl 4-t-butylphenol, each having the composition shown in Table 3 and were taken for testing.

TABLE 3

COMPOSITION OF CUTS A AND B FROM BUTYLATION OF 2,4- AND 2,5-XYLENOL

| Component (%) | A | B |
|---|---|---|
| 2,4-Dimethyl-6-t-butylphenol | 87.03 | 17.33 |
| 2,5-Dimethyl-6-t-butylphenol | 9.11 | 77.74 |
| Others | 3.86 | 4.93 |

EXAMPLE 4

2,3-xylenol was butylated as described in Example 1, the butylated product was collected in a fraction boiling at 135°–170° C. at 30 mm of mercury.

EXAMPLE 5

The suspension polymerization of vinyl chloride was carried out in a 50 gallon reactor having the following formula:

| | |
|---|---|
| Vinyl Chloride Monomer | 100 parts |
| Water | 150 parts |
| Hydroxypropyl methlcellulose | .05-.06 phm |
| di(2-ethylhexyl)peroxydicarbonate | .068-.085 phm |

When the polymerization reached 85% conversion to polyvinyl chloride as measured by pressure drop, a mixture of 0.029 parts per hundred monomer alpha methyl styrene and 0.057 parts per hundred monomer of polyvinyl chloride stabilizer was bombed into the reactor. The major portion of the unreacted VCM was removed from the reactor by venting. Steam was injected into the bottom of the reactor with the vent line open and the slurry temperature was thus increased to 225° F. Vacuum was applied to the reactor and the slurry was cooled to ambient temperature. The slurry was centrifuged and dried.

EXAMPLE 6

The heat stability of the resins from Example 5 was measured by preparing a mill blend consisting of the following recipe;

| | |
|---|---|
| Resin | 300 grams |
| Processing Aid (K120N) Trademark of and sold by Rohm and Haas | 9 grams |
| Wax (XL165) Trademark of and Sold by American Hoerst Co. | 1.5 grams |
| Calcium Stearate | 2.4 grams |
| Methyl tin mercaptide stabilizer (TM181) Trademark of and sold by Cincinnatti Milacron Co. | .91 grams |

The blend was placed on a heated 2 roll mill at about 385° F. Chips were removed from the mixture at 1 minute intervals beginning when the blend first banded on the mill. The test was stopped when the mill sheets turned reddish brown indicating severe degradation. All resins tested were compared to specially prepared control resin having no stabilizer added, by comparing the color of the resin chips to the 4 and 8 minute chips of the control resin. The values in the 4 and 8 columns of Table 3 show the times on the mill for the resin prepared with the PVC stabilizer described in Example 2 to reach equal color as the control resin at 4 and 8 minutes. The larger the value the more stable the resin was and conversely, the smaller the value the less stable the resin.

EXAMPLE 7

The polymerization described in Example 5 was carried out. Conventional hindered phenolic antioxidants (2,6-di-t-butyl-4-ethylphenol and 2,2'methylene bis(4-methyl-6-t-butylphenol) were used as polyvinyl chloride stabilizers. The mill heat stability results for these stabilizers are shown for comparative purposes in Table 4.

TABLE 4
MILL HEAT STABILITY
50 Gallon Reactor Polymerization

| PVC Stabilizer | MILL HEAT STABILITY | |
|---|---|---|
| | 4 | 8 |
| None | 3.0 | 6.5 |
| Example 2 | 6.0 | 10.0 |
| Butylated hydroxytoluene | 4.5 | 9.0 |
| 4,4'-Methylene bis(2,6-di-tert-butylphenol) | 3.0 | 8.0 |
| 2,6,-Di-tert-butyl-4-ethylphenol | 3.5 | 8.0 |
| 2,2'-Methylene bis(4-methyl-6-tert-butylphenol) | 4.0 | 8.0 |

EXAMPLE 8

Polymerizations were carried out in a 15 gallon reactor using the formulation shown in Example 5. At approximately 85% conversion a mixture of 0.110 parts per hundred monomer (phm) alpha methyl styrene and 0.051 parts per hundred monomer of the PVC stabilizers described in Examples 1, 3, and 4 were bombed into the reactor. The reactor was vented and the slurry was steam stripped as described in Example 5. Table 5 gives a mill heat stability results for the samples obtained. Comparisons were made on the 4 minute and 7 minute chips of the control resin.

The smaller reactor in Examples 8 and 9 produces a less stable resin and severe degradation occurred earlier in the test. Thus a direct comparison between the values obtained in Table 4 with those in Table 5 is not possible. Comparisons can be made only within each table.

EXAMPLE 9

The process described in Example 8 was carried out and a conventional hindered phenolic antioxidant (butylated hydroxytoluene or BHT) was used as a PVC stabilizer. The mill heat stability result is shown in Table 5.

TABLE 5
MILL HEAT STABILITY
15 Gallon Reactor Polymerization

| PVC Stabilizer | MILL HEAT STABILITY | |
|---|---|---|
| | 4 | 7 |
| Example 1, cut 2 | 4.5 | 8.0 |
| Example 1, cut 3 | 4.5 | 8.0 |
| Example 1, cut 4 | 4.5 | 8.0 |
| Example 3, cut A | 4.0 | 7.0 |
| Example 3, cut B | 4.0 | 7.0 |
| Example 4 | 3.5 | 7.0 |
| Butylated hydroxytoluene | 4.0 | 7.0 |

Examples 10 through 13 illustrate the effectiveness of the instant invention as a polyvinyl chloride shortstop agent.

EXAMPLE 10

A mixture of the product of phenolic methylation which distills at temperatures of from 205° C. to 230° C. at 1 atmosphere (200 grams) and 2,4,6-trimethylphenol (50 grams) was isobutylated in the presence of 10 milliliters of boron trifluoride etherate by passing isobutylene into the mixture at such a rate that the reaction temperature maintained an autogeneous temperature of 70° to 80° C. After 3 hours, the temperature began to fall and after 4 hours the reaction was stopped by terminating stirring and stopping isobutylene flow. After standing overnight, the reaction mixture was poured into 250 ml of water and then 20 to 30 ml of 50% aqueous sodium hydroxide was added (sufficient to bring the pH of the aqueous phase to greater than 10). After standing, the layers separated and the aqueous layer was discarded. The organic layer was washed with a fresh 500 ml portion of water. The organic phase was then separated, dried over anhydrous sodium sulfate and distilled.

The distillation was taken in four cuts described in Table 6 below. In the table, reflux ratio determines the percent of the fraction which came overhead as compared to the percent remaining in the condenser. Cuts 3 and 4 of the table were combined and used as described in Example 13.

TABLE 6

| Cut No. | Boiling Point °C. | Reflux Ratio % overhead/condenser | Weight of Cut (g) |
|---|---|---|---|
| 1 | Up to 150° atm. press. | 4/1 | 12.2 |
| 2 | Up to 110° @ 10 mm Hg | 1/1 | 86.7 |
| 3 | 110 to 120° @ | | |

TABLE 6-continued

| Cut No. | Boiling Point °C. | Reflux Ratio % overhead/condenser | Weight of Cut (g) |
|---|---|---|---|
| 4 | 120 to 165° @ 10 mm Hg | 1/1 | 68.0 |
|  | 10 mm Hg | 1/1 | 167.3 |
| Loss, hold-up residue | — |  | 8.5 |

EXAMPLE 11

A mixture of 1699 grams of a phenolic methylation product fraction described in Example 10, and 36 grams of boron trifluoride etherate were placed in the 3-liter flask fitted with a mechanical stirrer, glass inlet sparger, and reflux condenser connected to a gas boiler. Isobutylene was added as rapidly as comsumed causing the temperature to increase from 25° C. to 90° C. over a period of 1 hour. Isobutylene addition was continued for an additional hour after which time the flask had become so full no additional isobutylene could be added. After standing overnight the reaction mixture (2659 grams) was washed with water, made alkaline with a 5% sodium hydroxide solution and again washed with water. The organic phase was separated, dried over 150 grams of anhydrous potassium carbonate, and then fractionally distilled through a 3-foot packed column. The fractional cuts were made as described in Table 7 with cut 2 being used in Example 13.

TABLE 7

| Cut | Boiling Point at 30 mm Hg. | Weight (g) |
|---|---|---|
| 1 | 28–105° C. | 217.3 |
| 2 | 105–215° C. | 914.3 |
| Residue | — | 25.0 |
| Loss and hold-up |  | 75.4 |

EXAMPLE 12

A continuous backmixed reactor was utilized consisting of a 300 ml autoclave equipped with a feed inlet tube, a product stream outlet tube, and a 150 rpm catalyst basket packed with 16.9 grams of dry acidic catalyst (Amberlyst 15, a polystyrene crosslinked with divinylbenzene with sulfonic acid moieties attached to benzene rings, Trademark of and sold by Rohm and Haas). The steady state liquid volume in the reactor was 109 ml. A pressure of approximately 3 pounds per square inch gauge (psig) was maintained in the reactor during the run using a backpressure regulator. A feed consisting of 440 grams of isobutylene and 950 grams of a phenol methylation product fraction previously described was pumped at 1.1 to 1.4 ml per minute into the reactor. The reactor was maintained at a temperature between 74° and 92° C. Two additional charges of feed, each containing 950 grams of methylation fraction and 440 grams of isobutylene were pumped through the reactor at 0.7 to 0.9 ml per minute while the reactor was maintained at temperature. The methylation product fraction had the following approximate composition: 2,4-xylenol, 20.2%; 2,5-xylenol, 21.3%; 2,6-xylenol, 8.4%; 2,3-xylenol 19.7%; 2,3,6-trimethylphenol, 3.3%; 2,4,6-trimethylphenol, 23.6%; pentamethylbenzene 2.5%; phenol 0.1%; and cresol 0.9%. The product stream samples except for several small samples kept separate for analysis was combined to give a composite sample weighing 3,230 grams.

A portion of the above composite sample (363 grams) was fractionally distilled at 30 mm on a spinning band column. The portion of the distillate boiling at temperatures of from 120° to 188° C. at 30 mm of mercury was combined (total weight 264 grams).

EXAMPLE 13

Polyvinyl chloride polymerizations were carried out in an 8 gallon reactor using the following recipe;

| | |
|---|---|
| vinyl chloride monomer | 100 parts |
| Water | 180 parts |
| Hydroxypropyl methylcellulose | .099 phm |
| Di(2-ethylhexyl) peroxydicarbonate | .099 phm |

When the reaction reached approximately 85% conversion of vinyl chloride to polyvinyl chloride, as measured by reactor pressure, the experimental shortstop agents were bombed into the reactor. Pressurized water was used to push the shortstop agent into the reactor so as not to introduce any air or gas which would alter the reactor pressure. The unreacted vinyl chloride monomer, (approximately 15% of the charge) was left in the sealed reactor. The reactor was then heated to 180° F. and maintained for 1 hour.

A pressure profile was used to evaluate the effectiveness of the shortstopping agents. When free radicals were terminated, the pressure increased with temperature and did not appreciably decrease during the 1 hour heating at 180° F. Agents for free radical termination which were less effective, showed a similar pressure increase initially, but a pressure decrease followed fairly rapidly as further polymerization took place during the 1 hour period at 180° F.

The results are shown in Table 8 below wherein maximum pressure is the pressure obtained during the 1 hour at 180° F. and minimum pressure is the pressure at the end of the 1 hour heating period.

TABLE 8

| Termination Agent | PHM[1] | PRESSURE AT 180° F. (PSIG) Max. | Min. |
|---|---|---|---|
| α-methyl styrene | .055 | 152 | 145 |
| Butylated hydroxytoluene | .028 | 145 | 133 |
| Butylated hydroxytoluene | .055 | 146 | 144 |
| 2,6-Di-t-butyl-4-n-butyl-phenol | .055 | 133 | 109 |
| 2,4-Di-t-nonyl-6-methyl-phenol | .055 | 141 | 126 |
| 8-Quinolinol | .028 | 139 | 116 |
| 8-Quinolinol | .055 | 145 | 124 |
| Thiosemicarbazide | .055 | 152 | 150 |
| Hydroquinone | .028 | 144 | 117 |
| Example 12 | .028 | 140 | 136 |
| Example 12 | .055 | 152 | 143 |
| Example 11 | .055 | 155 | 151 |
| Example 12 | .055 | 154 | 154 |

[1]parts per hundred monomer

While certain embodiments and details have been shown for the purpose of illustrating this invention, it will be apparent to those skilled in this art that various changes and modifications may be made herein without departing from the spirit or scope of the invention.

We claim:

1. A method for terminating polyvinyl chloride polymerizations comprising injecting into the polymerization reactor at the desired level of conversion a free radical inhibitor obtained by,
- (1) methylating phenol with methanol in vapor phase at pressures of from about 1 to about 2500 pounds per square inch gauge, temperatures of from about 400° C. to about 700° C. and liquid hourly space velocity of from about 1 to about 15 in the presence of alumina or alumina containing catalyst and recovering a product stream therefrom;
- (2) distilling said product stream into desired fractions and retaining the fraction obtained at temperatures of from about 205° C. to about 230° C. at one atmosphere, and then;
- (3) alkylating the retained fraction with acidic catalysts at temperatures of from about 10° C. to about 110° C. and pressures of at least atmospheric while at a product fraction/alkylating agent weight ratio of from about 1/0.23 to about 1/1.85 respectively, then;
- (4) fractionally distilling the product of (3) and retaining the fraction obtained at temperatures of from about 110° C. to about 200° C. at 30 mm of mercury.

2. A method as described in claim 1 wherein the free radical inhibitor is obtained by methylating phenol at pressures of from 10 to 50 pounds per square inch gauge and LHSV of 1 to about 5.

3. A method as described in claim 1 wherein the inhibitor is obtained using a process wherein the acidic catalyst of (3) is selected from the group consisting of sulfuric acid, sulfonated polystyrene resin crosslinked with divinylbenzene, boron trifluoride etherate, and benzene sulfonic acid.

4. A method as described in claim 3 wherein the inhibitor is obtained from alkylating the retained fraction of (3) with a material selected from the group consisting of isobutylene, isopentylene, isohexene, isooctene, cyclopentene, and cyclooctene.

* * * * *